(12) United States Patent
Allen et al.

(10) Patent No.: US 10,380,251 B2
(45) Date of Patent: Aug. 13, 2019

(54) MINING NEW NEGATION TRIGGERS DYNAMICALLY BASED ON STRUCTURED AND UNSTRUCTURED KNOWLEDGE

(71) Applicant: International Business Machines Corporation, Armonk, NY (US)

(72) Inventors: Corville O. Allen, Morrisville, NC (US); Roberto DeLima, Apex, NC (US); Aysu Ezen Can, Cary, NC (US); Robert C. Sizemore, Fuquay-Varina, NC (US)

(73) Assignee: International Business Machines Corporation, Armonk, NY (US)

( * ) Notice: Subject to any disclaimer, the term of this patent is extended or adjusted under 35 U.S.C. 154(b) by 104 days.

(21) Appl. No.: 15/261,328

(22) Filed: Sep. 9, 2016

(65) Prior Publication Data

US 2018/0075012 A1 Mar. 15, 2018

(51) Int. Cl.
*G06F 17/27* (2006.01)
*G16H 10/60* (2018.01)

(52) U.S. Cl.
CPC ........ *G06F 17/278* (2013.01); *G06F 17/2785* (2013.01); *G16H 10/60* (2018.01)

(58) Field of Classification Search
CPC ............... G06F 17/2735; G06F 17/278; G06F 17/2785; G06F 19/322; G06F 17/271; G16H 10/60
See application file for complete search history.

(56) References Cited

U.S. PATENT DOCUMENTS 8,239,189 B2 * 8/2012 Skubacz ............. G06F 17/2785
704/10
8,275,803 B2 9/2012 Brown et al.
(Continued)

OTHER PUBLICATIONS

Blanco, Eduardo et al., "Some Issues on Detecting Negation from Text", Association for the Advancement of Artificial Intelligence, Proceedings of the Twenty-Fourth International Florida Artificial Intelligence Research Society Conference, Mar. 20, 2011, pp. 228-233.

(Continued)

*Primary Examiner* — Angela A Armstrong
(74) *Attorney, Agent, or Firm* — Stephen R. Tkacs; Stephen J. Walder, Jr.; Reza Sarbakhsh

(57) ABSTRACT

A mechanism is provided in a data processing system comprising at least one processor and at least one memory, the at least one memory comprising instructions executed by the at least one processor to cause the at least one processor to implement a cognitive natural language processing system. The cognitive natural language processing (NLP) system analyzes a portion of natural language text to identify an attribute specified in the natural language text. The cognitive NLP system analyzes the portion of natural language text to determine whether a known negation trigger is present in the natural language text in association with the attribute. In response to determining that the natural language text does not contain a known negation trigger in association with the attribute, the cognitive NLP system determines whether the attribute is negated based on instances of the attribute in other natural language content similar to the natural language text. In response to determining that the attribute is negated, the cognitive NLP system identifies a new negation trigger associated with the attribute in the natural language text. The cognitive NLP system stores the new negation (Continued)

trigger in association with the attribute in a negation trigger dictionary data structure.

14 Claims, 5 Drawing Sheets

(56) References Cited

U.S. PATENT DOCUMENTS

| | | | |
|---|---|---|---|
| 8,412,530 | B2 | 4/2013 | Pereg et al. |
| 8,639,497 | B2 * | 1/2014 | Eggebraaten ............ G06F 17/28 704/257 |
| 9,092,514 | B2 | 7/2015 | Cardie et al. |
| 9,201,860 | B1 | 12/2015 | Zhang et al. |
| 9,201,868 | B1 | 12/2015 | Zhang et al. |
| 9,244,910 | B2 * | 1/2016 | Miura ................. G06F 17/2785 |
| 9,275,041 | B2 * | 3/2016 | Ghosh ................. G06F 17/2785 |
| 9,799,035 | B2 * | 10/2017 | Cama ..................... G06Q 30/00 |
| 9,881,000 | B1 * | 1/2018 | Jones .................. G06F 17/2785 |
| 2008/0249764 | A1 | 10/2008 | Huang et al. |
| 2009/0265307 | A1 | 10/2009 | Reisman et al. |
| 2009/0287678 | A1 | 11/2009 | Brown et al. |
| 2011/0066587 | A1 | 3/2011 | Ferrucci et al. |
| 2011/0125734 | A1 | 5/2011 | Duboue et al. |
| 2012/0254063 | A1 | 10/2012 | Ritterman et al. |
| 2012/0278102 | A1 | 11/2012 | Johnson |
| 2013/0007055 | A1 | 1/2013 | Brown et al. |
| 2013/0018652 | A1 | 1/2013 | Ferrucci et al. |
| 2013/0018892 | A1 | 1/2013 | Castellanos et al. |
| 2013/0066886 | A1 | 3/2013 | Bagchi et al. |
| 2014/0012863 | A1 | 1/2014 | Sundaresan et al. |
| 2014/0095186 | A1 * | 4/2014 | Gotz ................. G06Q 10/0635 705/2 |
| 2015/0073774 | A1 * | 3/2015 | Becker ................ G06F 17/2785 704/9 |
| 2015/0106079 | A1 | 4/2015 | Bostick et al. |
| 2015/0379241 | A1 | 12/2015 | Furst et al. |
| 2016/0098394 | A1 | 4/2016 | Bruno et al. |

OTHER PUBLICATIONS

Chapman, Wendy W. et al., "ConText: An Algorithm for Identifying Contextual Features from Clinical Text", Association for Computational Linguistics, BioNLP 2007: Biological, translational, and clinical language processing, Prague, Jun. 2007, pp. 81-88.

Councill, Isaac G. et al., "What's Great and What's Not: Learning to Classify the Scope of Negation for improved Sentiment Analysis", Proceedings of the Workshop on Negation and Speculation in Natural Language Processing, Uppsala, Sweden, Jul. 2010, pp. 51-59.

Dalianis, Hercules et al., "Creating and Evaluating a Consensus for Negated and Speculative Words in a Swedish Clinical Corpus", Proceedings of the Workshop on Negation and Speculation in Natural Language Processing, Uppsala, Sweden, Jul. 2010, pp. 5-13.

Goldstein, Ira et al., "Does Negation Really Matter?", Proceedings of the Workshop on Negation and Speculation in Natural Language Processing, Uppsala, Sweden, Jul. 2010, pp. 23-27.

Goryachev J, Sergey et al., "Implementation and Evaluation of Four Different Methods of Negation Detection", DSG, Boston, Technical report, 2006 (month unknown), 6 pages.

High, Rob, "The Era of Cognitive Systems: An Inside Look at IBM Watson and How it Works", IBM Corporation, Redbooks, Dec. 12, 2012, 16 pages.

Liakata, Maria, "Zones of conceptualisation in scientific papers: a window to negative and speculative statements", Proceedings of the Workshop on Negation and Speculation in Natural Language Processing, Uppsala, Sweden, Jul. 2010, pp. 1-4.

McCord, M.C. et al., "Deep parsing in Watson", IBM J. Res. & Dev. vol. 56 No. 3/4 Paper 3, May/Jul. 2012, pp. 3:1-3:15.

Velupillai, Sumithra, "Towards A Better Understanding of Uncertainties and Speculations in Swedish Clinical Text—Analysis of an Initial Annotation Trial", Proceedings of the Workshop on Negation and Speculation in Natural Language Processing, Uppsala, Sweden, Jul. 2010, pp. 14-22.

Vincze, Veronika, "Speculation and negation annotation in natural language texts: what the case of BioScope might (not) reveal", Proceedings of the Workshop on Negation and Speculation in Natural Language Processing, Uppsala, Sweden, Jul. 2010, pp. 28-31.

Wu, Stephen et al., "Negation's Not Solved: Generalizability Versus Optimizability in Clinical Natural Language Processing", The MITRE Corporation, Approved for Public Release; Distribution Unlimited. 134469, 2013 (month unknown), 17 pages.

Yuan, Michael J., "Watson and healthcare, How natural language processing and semantic search could revolutionize clinical decision support", IBM developerWorks, IBM Corporation, Apr. 12, 2011, 14 pages.

\* cited by examiner

MINING NEW NEGATION TRIGGERS DYNAMICALLY BASED ON STRUCTURED AND UNSTRUCTURED KNOWLEDGE

BACKGROUND

The present application relates generally to an improved data processing apparatus and method and more specifically to mechanisms for dynamically mining new negation triggers based on structured and unstructured knowledge.

Decision-support systems exist in many different industries where human experts require assistance in retrieving and analyzing information. An example that will be used throughout this application is a diagnosis system employed in the healthcare industry. Diagnosis systems can be classified into systems that use structured knowledge, systems that use unstructured knowledge, and systems that use clinical decision formulas, rules, trees, or algorithms. The earliest diagnosis systems used structured knowledge or classical, manually constructed knowledge bases. The Internist-I system developed in the 1970s uses disease-finding relations and disease-disease relations. The MYCIN system for diagnosing infectious diseases, also developed in the 1970s, uses structured knowledge in the form of production rules, stating that if certain facts are true, then one can conclude certain other facts with a given certainty factor. DXplain, developed starting in the 1980s, uses structured knowledge similar to that of Internist-I, but adds a hierarchical lexicon of findings.

Iliad, developed starting in the 1990s, adds more sophisticated probabilistic reasoning where each disease has an associated a priori probability of the disease (in the population for which Iliad was designed), and a list of findings along with the fraction of patients with the disease who have the finding (sensitivity), and the fraction of patients without the disease who have the finding (1-specificity).

In 2000, diagnosis systems using unstructured knowledge started to appear. These systems use some structuring of knowledge such as, for example, entities such as findings and disorders being tagged in documents to facilitate retrieval. ISABEL, for example, uses Autonomy information retrieval software and a database of medical textbooks to retrieve appropriate diagnoses given input findings. Autonomy Auminence uses the Autonomy technology to retrieve diagnoses given findings and organizes the diagnoses by body system. First CONSULT allows one to search a large collection of medical books, journals, and guidelines by chief complaints and age group to arrive at possible diagnoses. PEPID DDX is a diagnosis generator based on PEPID's independent clinical content.

Clinical decision rules have been developed for a number of medical disorders, and computer systems have been developed to help practitioners and patients apply these rules. The Acute Cardiac Ischemia Time-Insensitive Predictive Instrument (ACI-TIPI) takes clinical and ECG features as input and produces probability of acute cardiac ischemia as output to assist with triage of patients with chest pain or other symptoms suggestive of acute cardiac ischemia. ACI-TIPI is incorporated into many commercial heart monitors/defibrillators. The CaseWalker system uses a four-item questionnaire to diagnose major depressive disorder. The PKC Advisor provides guidance on 98 patient problems such as abdominal pain and vomiting.

SUMMARY

This Summary is provided to introduce a selection of concepts in a simplified form that are further described herein in the Detailed Description. This Summary is not intended to identify key factors or essential features of the claimed subject matter, nor is it intended to be used to limit the scope of the claimed subject matter.

In one illustrative embodiment, a method is provided in a data processing system comprising at least one processor and at least one memory, the at least one memory comprising instructions executed by the at least one processor to cause the at least one processor to implement a cognitive natural language processing system. The method comprises analyzing, by the cognitive natural language processing (NLP) system, a portion of natural language text to identify an attribute specified in the natural language text. The method further comprises analyzing, by the cognitive NLP system, the portion of natural language text to determine whether a known negation trigger is present in the natural language text in association with the attribute. The method further comprises determining, by the cognitive NLP system, whether the attribute is negated based on instances of the attribute in other natural language content similar to the natural language text in response to determining that the natural language text does not contain a known negation trigger in association with the attribute. The method further comprises identifying, by the cognitive NLP system, a new negation trigger associated with the attribute in the natural language text in response to determining that the attribute is negated. The method further comprises storing, by the cognitive NLP system, the new negation trigger in association with the attribute in a negation trigger dictionary data structure.

In other illustrative embodiments, a computer program product comprising a computer usable or readable medium having a computer readable program is provided. The computer readable program, when executed on a computing device, causes the computing device to perform various ones of, and combinations of, the operations outlined above with regard to the method illustrative embodiment.

In yet another illustrative embodiment, a system/apparatus is provided. The system/apparatus may comprise one or more processors and a memory coupled to the one or more processors. The memory may comprise instructions which, when executed by the one or more processors, cause the one or more processors to perform various ones of, and combinations of, the operations outlined above with regard to the method illustrative embodiment.

These and other features and advantages of the present invention will be described in, or will become apparent to those of ordinary skill in the art in view of, the following detailed description of the example embodiments of the present invention.

BRIEF DESCRIPTION OF THE DRAWINGS

The invention, as well as a preferred mode of use and further objectives and advantages thereof, will best be understood by reference to the following detailed description of illustrative embodiments when read in conjunction with the accompanying drawings, wherein.

DETAILED DESCRIPTION

Figure 1:
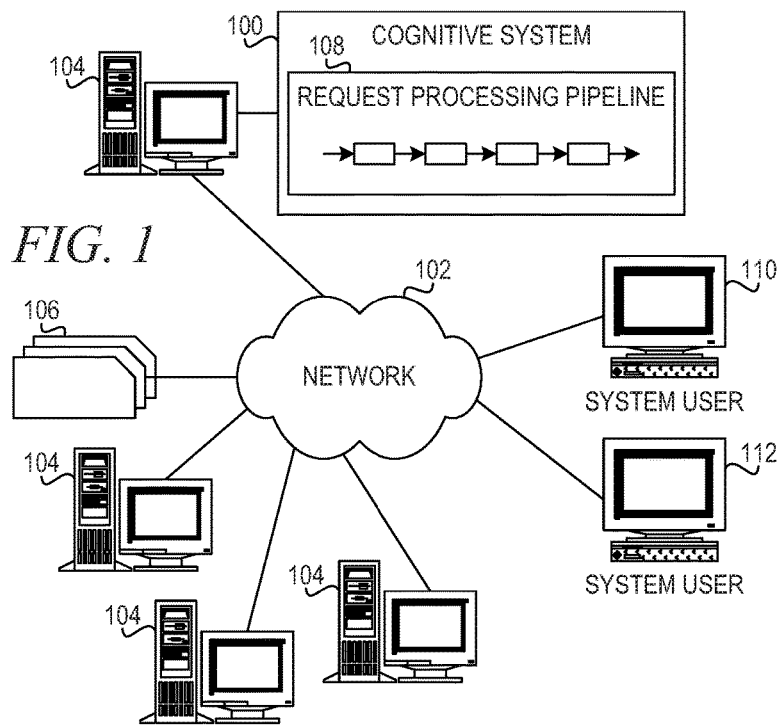
FIG. 1 depicts a schematic diagram of one illustrative embodiment of a cognitive system in a computer network.

For improving accuracy in natural language processing, it is crucial for cognitive systems to understand which phrases are negated and which are not. Particularly in the medical domain, text has a lot of negated phrases interleaved with non-negated phrases. Most of the time, negated and non-negated clauses occur in the same sentences, making it difficult to apply a naïve algorithm to differentiate those two categories. In a clinical decision support system, it is very important to extract information about patients correctly so as to make successful predictions or aid in decisions. For instance, if an electronic medical record (EMR) mentions non-existence of a specific symptom, treating that phase as if the symptom was present would lead to wrong treatment recommendations. The illustrative embodiments classify sentences according to negation status in clinical text.

The embodiments are described below with reference to a question answering (QA) system; however, aspects of the illustrative embodiments may apply to other embodiments, such as decision support systems, analytics, data visualization, social media, search engine indexing, etc. The embodiments are described with respect to the medical domain, in particular electronic medical records; however, aspects of the embodiments may apply in other domains and other types of documents with structured and unstructured content. Application of aspects of the illustrative embodiments to other embodiments is within the scope of the present invention.

Before beginning the discussion of the various aspects of the illustrative embodiments in more detail, it should first be appreciated that throughout this description the term "mechanism" will be used to refer to elements of the present invention that perform various operations, functions, and the like. A "mechanism," as the term is used herein, may be an implementation of the functions or aspects of the illustrative embodiments in the form of an apparatus, a procedure, or a computer program product. In the case of a procedure, the procedure is implemented by one or more devices, apparatus, computers, data processing systems, or the like. In the case of a computer program product, the logic represented by computer code or instructions embodied in or on the computer program product is executed by one or more hardware devices in order to implement the functionality or perform the operations associated with the specific "mechanism." Thus, the mechanisms described herein may be implemented as specialized hardware, software executing on general purpose hardware, software instructions stored on a medium such that the instructions are readily executable by specialized or general purpose hardware, a procedure or method for executing the functions, or a combination of any of the above.

The present description and claims may make use of the terms "a," "at least one of," and "one or more of" with regard to particular features and elements of the illustrative embodiments. It should be appreciated that these terms and phrases are intended to state that there is at least one of the particular feature or element present in the particular illustrative embodiment, but that more than one can also be present. That is, these terms/phrases are not intended to limit the description or claims to a single feature/element being present or require that a plurality of such features/elements be present. To the contrary, these terms/phrases only require at least a single feature/element with the possibility of a plurality of such features/elements being within the scope of the description and claims.

Moreover, it should be appreciated that the use of the term "engine," if used herein with regard to describing embodiments and features of the invention, is not intended to be limiting of any particular implementation for accomplishing and/or performing the actions, steps, processes, etc., attributable to and/or performed by the engine. An engine may be, but is not limited to, software, hardware and/or firmware or any combination thereof that performs the specified functions including, but not limited to, any use of a general and/or specialized processor in combination with appropriate software loaded or stored in a machine readable memory and executed by the processor. Further, any name associated with a particular engine is, unless otherwise specified, for purposes of convenience of reference and not intended to be limiting to a specific implementation. Additionally, any functionality attributed to an engine may be equally performed by multiple engines, incorporated into and/or combined with the functionality of another engine of the same or different type, or distributed across one or more engines of various configurations.

In addition, it should be appreciated that the following description uses a plurality of various examples for various elements of the illustrative embodiments to further illustrate example implementations of the illustrative embodiments and to aid in the understanding of the mechanisms of the illustrative embodiments. These examples are intended to be non-limiting and are not exhaustive of the various possibilities for implementing the mechanisms of the illustrative embodiments. It will be apparent to those of ordinary skill in the art in view of the present description that there are many other alternative implementations for these various elements that may be utilized in addition to, or in replacement of, the examples provided herein without departing from the spirit and scope of the present invention.

The illustrative embodiments may be utilized in many different types of data processing environments. In order to provide a context for the description of the specific elements and functionality of the illustrative embodiments, FIGS. 1-4 are provided hereafter as example environments in which aspects of the illustrative embodiments may be implemented. It should be appreciated that FIGS. 1-4 are only examples and are not intended to assert or imply any limitation with regard to the environments in which aspects or embodiments of the present invention may be implemented. Many modifications to the depicted environments may be made without departing from the spirit and scope of the present invention.

FIGS. 1-4 are directed to describing an example cognitive system for healthcare applications (also referred to herein as a "healthcare cognitive system") which implements a request processing pipeline, such as a Question Answering (QA) pipeline (also referred to as a Question/Answer pipeline or Question and Answer pipeline) for example, request processing methodology, and request processing computer program product with which the mechanisms of the illustrative embodiments are implemented. These requests may be provided as structure or unstructured request messages, natural language questions, or any other suitable format for requesting an operation to be performed by the healthcare cognitive system. As described in more detail hereafter, the particular healthcare application that is implemented in the cognitive system of the present invention is a healthcare application for providing medical treatment recommendations for patients based on their specific features as obtained from various sources, e.g., patient electronic medical records (EMRs), patient questionnaires, etc. In particular, the mechanisms of the present invention provide a mechanism for dynamically mining new negation triggers based on structured and unstructured knowledge.

It should be appreciated that the healthcare cognitive system, while shown as having a single request processing pipeline in the examples hereafter, may in fact have multiple request processing pipelines. Each request processing pipeline may be separately trained and/or configured to process requests associated with different domains or be configured to perform the same or different analysis on input requests (or questions in implementations using a QA pipeline), depending on the desired implementation. For example, in some cases, a first request processing pipeline may be trained to operate on input requests directed to a first medical malady domain (e.g., various types of blood diseases) while another request processing pipeline may be trained to answer input requests in another medical malady domain (e.g., various types of cancers). In other cases, for example, the request processing pipelines may be configured to provide different types of cognitive functions or support different types of healthcare applications, such as one request processing pipeline being used for patient diagnosis, another request processing pipeline being configured for medical treatment recommendation, another request processing pipeline being configured for patient monitoring, etc.

Moreover, each request processing pipeline may have its own associated corpus or corpora that they ingest and operate on, e.g., one corpus for blood disease domain documents and another corpus for cancer diagnostics domain related documents in the above examples. In some cases, the request processing pipelines may each operate on the same domain of input questions but may have different configurations, e.g., different annotators or differently trained annotators, such that different analysis and potential answers are generated. The healthcare cognitive system may provide additional logic for routing input questions to the appropriate request processing pipeline, such as based on a determined domain of the input request, combining and evaluating final results generated by the processing performed by multiple request processing pipelines, and other control and interaction logic that facilitates the utilization of multiple request processing pipelines.

As noted above, one type of request processing pipeline with which the mechanisms of the illustrative embodiments may be utilized is a Question Answering (QA) pipeline. The description of example embodiments of the present invention hereafter will utilize a QA pipeline as an example of a request processing pipeline that may be augmented to include mechanisms in accordance with one or more illustrative embodiments. It should be appreciated that while the present invention will be described in the context of the cognitive system implementing one or more QA pipelines that operate on an input question, the illustrative embodiments are not limited to such. Rather, the mechanisms of the illustrative embodiments may operate on requests that are not posed as "questions" but are formatted as requests for the cognitive system to perform cognitive operations on a specified set of input data using the associated corpus or corpora and the specific configuration information used to configure the cognitive system. For example, rather than asking a natural language question of "What diagnosis applies to patient P?" the cognitive system may instead receive a request of "generate diagnosis for patient P," or the like. It should be appreciated that the mechanisms of the QA system pipeline may operate on requests in a similar manner to that of input natural language questions with minor modifications. In fact, in some cases, a request may be converted to a natural language question for processing by the QA system pipelines if desired for the particular implementation.

As will be discussed in greater detail hereafter, the illustrative embodiments may be integrated in, augment, and extend the functionality of these QA pipeline, or request processing pipeline, mechanisms of a healthcare cognitive system with regard to providing a medical malady independent treatment recommendation system which may receive an input question regarding the recommended treatment for a specific patient and may utilize the QA pipeline mechanisms to evaluate patient information and other medical information in one or more corpora of medical information to determine the most appropriate treatment for the specific patient.

Thus, it is important to first have an understanding of how cognitive systems and question and answer creation in a cognitive system implementing a QA pipeline is implemented before describing how the mechanisms of the illustrative embodiments are integrated in and augment such cognitive systems and request processing pipeline, or QA pipeline, mechanisms. It should be appreciated that the mechanisms described in FIGS. 1-4 are only examples and are not intended to state or imply any limitation with regard to the type of cognitive system mechanisms with which the illustrative embodiments are implemented. Many modifications to the example cognitive system shown in FIGS. 1-4 may be implemented in various embodiments of the present invention without departing from the spirit and scope of the present invention.

As an overview, a cognitive system is a specialized computer system, or set of computer systems, configured with hardware and/or software logic (in combination with hardware logic upon which the software executes) to emulate human cognitive functions. These cognitive systems apply human-like characteristics to conveying and manipulating ideas which, when combined with the inherent strengths of digital computing, can solve problems with high accuracy and resilience on a large scale. A cognitive system performs one or more computer-implemented cognitive operations that approximate a human thought process as well as enable people and machines to interact in a more natural manner so as to extend and magnify human expertise and cognition. A cognitive system comprises artificial intelligence logic, such as natural language processing (NLP) based logic, for example, and machine learning logic, which may be provided as specialized hardware, software executed on hardware, or any combination of specialized hardware and software executed on hardware. The logic of the cognitive system implements the cognitive operation(s), examples of which include, but are not limited to, question answering, identification of related concepts within different portions of content in a corpus, intelligent search algorithms, such as Internet web page searches, for example, medical diagnostic and treatment recommendations, and other types of recommendation generation, e.g., items of interest to a particular user, potential new contact recommendations, or the like.

IBM Watson™ is an example of one such cognitive system which can process human readable language and identify inferences between text passages with human-like high accuracy at speeds far faster than human beings and on a larger scale. In general, such cognitive systems are able to perform the following functions:

- Navigate the complexities of human language and understanding
- Ingest and process vast amounts of structured and unstructured data
- Generate and evaluate hypothesis
- Weigh and evaluate responses that are based only on relevant evidence
- Provide situation-specific advice, insights, and guidance
- Improve knowledge and learn with each iteration and interaction through machine learning processes
- Enable decision making at the point of impact (contextual guidance)
- Scale in proportion to the task
- Extend and magnify human expertise and cognition
- Identify resonating, human-like attributes and traits from natural language
- Deduce various language specific or agnostic attributes from natural language
- High degree of relevant recollection from data points (images, text, voice) (memorization and recall)
- Predict and sense with situational awareness that mimic human cognition based on experiences
- Answer questions based on natural language and specific evidence In one aspect, cognitive systems provide mechanisms for answering questions posed to these cognitive systems using a Question Answering pipeline or system (QA system) and/or process requests which may or may not be posed as natural language questions. The QA pipeline or system is an artificial intelligence application executing on data processing hardware that answers questions pertaining to a given subject-matter domain presented in natural language. The QA pipeline receives inputs from various sources including input over a network, a corpus of electronic documents or other data, data from a content creator, information from one or more content users, and other such inputs from other possible sources of input. Data storage devices store the corpus of data. A content creator creates content in a document for use as part of a corpus of data with the QA pipeline. The document may include any file, text, article, or source of data for use in the QA system. For example, a QA pipeline accesses a body of knowledge about the domain, or subject matter area, e.g., financial domain, medical domain, legal domain, etc., where the body of knowledge (knowledgebase) can be organized in a variety of configurations, e.g., a structured repository of domain-specific information, such as ontologies, or unstructured data related to the domain, or a collection of natural language documents about the domain.

Content users input questions to cognitive system which implements the QA pipeline. The QA pipeline then answers the input questions using the content in the corpus of data by evaluating documents, sections of documents, portions of data in the corpus, or the like. When a process evaluates a given section of a document for semantic content, the process can use a variety of conventions to query such document from the QA pipeline, e.g., sending the query to the QA pipeline as a well-formed question which is then interpreted by the QA pipeline and a response is provided containing one or more answers to the question. Semantic content is content based on the relation between signifiers, such as words, phrases, signs, and symbols, and what they stand for, their denotation, or connotation. In other words, semantic content is content that interprets an expression, such as by using Natural Language Processing.

As will be described in greater detail hereafter, the QA pipeline receives an input question, parses the question to extract the major features of the question, uses the extracted features to formulate queries, and then applies those queries to the corpus of data. Based on the application of the queries to the corpus of data, the QA pipeline generates a set of hypotheses, or candidate answers to the input question, by looking across the corpus of data for portions of the corpus of data that have some potential for containing a valuable response to the input question. The QA pipeline then performs deep analysis on the language of the input question and the language used in each of the portions of the corpus of data found during the application of the queries using a variety of reasoning algorithms. There may be hundreds or even thousands of reasoning algorithms applied, each of which performs different analysis, e.g., comparisons, natural language analysis, lexical analysis, or the like, and generates a score. For example, some reasoning algorithms may look at the matching of terms and synonyms within the language of the input question and the found portions of the corpus of data. Other reasoning algorithms may look at temporal or spatial features in the language, while others may evaluate the source of the portion of the corpus of data and evaluate its veracity.

The scores obtained from the various reasoning algorithms indicate the extent to which the potential response is inferred by the input question based on the specific area of focus of that reasoning algorithm. Each resulting score is then weighted against a statistical model. The statistical model captures how well the reasoning algorithm performed at establishing the inference between two similar passages for a particular domain during the training period of the QA pipeline. The statistical model is used to summarize a level of confidence that the QA pipeline has regarding the evidence that the potential response, i.e. candidate answer, is inferred by the question. This process is repeated for each of the candidate answers until the QA pipeline identifies candidate answers that surface as being significantly stronger than others and thus, generates a final answer, or ranked set of answers, for the input question.

As mentioned above, QA pipeline mechanisms operate by accessing information from a corpus of data or information (also referred to as a corpus of content), analyzing it, and then generating answer results based on the analysis of this data. Accessing information from a corpus of data typically includes: a database query that answers questions about what is in a collection of structured records, and a search that delivers a collection of document links in response to a query against a collection of unstructured data (text, markup language, etc.). Conventional question answering systems are capable of generating answers based on the corpus of data and the input question, verifying answers to a collection of questions for the corpus of data, correcting errors in digital text using a corpus of data, and selecting answers to questions from a pool of potential answers, i.e. candidate answers.

Content creators, such as article authors, electronic document creators, web page authors, document database creators, and the like, determine use cases for products, solutions, and services described in such content before writing their content. Consequently, the content creators know what questions the content is intended to answer in a particular topic addressed by the content. Categorizing the questions, such as in terms of roles, type of information, tasks, or the like, associated with the question, in each document of a corpus of data allows the QA pipeline to more quickly and efficiently identify documents containing content related to a specific query. The content may also answer other questions that the content creator did not contemplate that may be useful to content users. The questions and answers may be verified by the content creator to be contained in the content for a given document. These capabilities contribute to improved accuracy, system performance, machine learning, and confidence of the QA pipeline. Content creators, automated tools, or the like, annotate or otherwise generate metadata for providing information useable by the QA pipeline to identify these question and answer attributes of the content.

Operating on such content, the QA pipeline generates answers for input questions using a plurality of intensive analysis mechanisms which evaluate the content to identify the most probable answers, i.e. candidate answers, for the input question. The most probable answers are output as a ranked listing of candidate answers ranked according to their relative scores or confidence measures calculated during evaluation of the candidate answers, as a single final answer having a highest ranking score or confidence measure, or which is a best match to the input question, or a combination of ranked listing and final answer.

FIG. 1 depicts a schematic diagram of one illustrative embodiment of a cognitive system 100 implementing a request processing pipeline 108, which in some embodiments may be a question answering (QA) pipeline, in a computer network 102. For purposes of the present description, it will be assumed that the request processing pipeline 108 is implemented as a QA pipeline that operates on structured and/or unstructured requests in the form of input questions. One example of a question processing operation which may be used in conjunction with the principles described herein is described in U.S. Patent Application Publication No. 2011/0125734, which is herein incorporated by reference in its entirety.

The cognitive system 100 is implemented on one or more computing devices 104 (comprising one or more processors and one or more memories, and potentially any other computing device elements generally known in the art including buses, storage devices, communication interfaces, and the like) connected to the computer network 102. The network 102 includes multiple computing devices 104 in communication with each other and with other devices or components via one or more wired and/or wireless data communication links, where each communication link comprises one or more of wires, routers, switches, transmitters, receivers, or the like. The cognitive system 100 and network 102 enables question processing and answer generation (QA) functionality for one or more cognitive system users via their respective computing devices 110-112. Other embodiments of the cognitive system 100 may be used with components, systems, sub-systems, and/or devices other than those that are depicted herein.

The cognitive system 100 is configured to implement a QA pipeline 108 that receive inputs from various sources. For example, the cognitive system 100 receives input from the network 102, a corpus of electronic documents 106, cognitive system users, and/or other data and other possible sources of input. In one embodiment, some or all of the inputs to the cognitive system 100 are routed through the network 102. The various computing devices 104 on the network 102 include access points for content creators and QA system users. Some of the computing devices 104 include devices for a database storing the corpus of data 106 (which is shown as a separate entity in FIG. 1 for illustrative purposes only). Portions of the corpus of data 106 may also be provided on one or more other network attached storage devices, in one or more databases, or other computing devices not explicitly shown in FIG. 1. The network 102 includes local network connections and remote connections in various embodiments, such that the cognitive system 100 may operate in environments of any size, including local and global, e.g., the Internet.

In one embodiment, the content creator creates content in a document of the corpus of data 106 for use as part of a corpus of data with the cognitive system 100. The document includes any file, text, article, or source of data for use in the cognitive system 100. QA system users access the cognitive system 100 via a network connection or an Internet connection to the network 102, and input questions to the cognitive system 100 that are answered by the content in the corpus of data 106. In one embodiment, the questions are formed using natural language. The cognitive system 100 parses and interprets the question via a QA pipeline 108, and provides a response to the cognitive system user, e.g., cognitive system user 110, containing one or more answers to the question. In some embodiments, the cognitive system 100 provides a response to users in a ranked list of candidate answers while in other illustrative embodiments, the cognitive system 100 provides a single final answer or a combination of a final answer and ranked listing of other candidate answers.

The cognitive system 100 implements the QA pipeline 108 which comprises a plurality of stages for processing an input question and the corpus of data 106. The QA pipeline 108 generates answers for the input question based on the processing of the input question and the corpus of data 106. The QA pipeline 108 will be described in greater detail hereafter with regard to FIG. 4.

In some illustrative embodiments, the cognitive system 100 may be the IBM Watson™ cognitive system available from International Business Machines Corporation of Armonk, N.Y., which is augmented with the mechanisms of the illustrative embodiments described hereafter. As outlined previously, a QA pipeline of the IBM Watson™ cognitive system receives an input question which it then parses to extract the major features of the question, which in turn are then used to formulate queries that are applied to the corpus of data. Based on the application of the queries to the corpus of data, a set of hypotheses, or candidate answers to the input question, are generated by looking across the corpus of data for portions of the corpus of data that have some potential for containing a valuable response to the input question. The QA pipeline of the IBM Watson™ cognitive system then performs deep analysis on the language of the input question and the language used in each of the portions of the corpus of data found during the application of the queries using a variety of reasoning algorithms.

The scores obtained from the various reasoning algorithms are then weighted against a statistical model that summarizes a level of confidence that the QA pipeline of the IBM Watson™ cognitive system has regarding the evidence that the potential response, i.e. candidate answer, is inferred by the question. This process is be repeated for each of the candidate answers to generate ranked listing of candidate answers which may then be presented to the user that submitted the input question, or from which a final answer is selected and presented to the user. More information about the QA pipeline of the IBM Watson™ cognitive system may be obtained, for example, from the IBM Corporation website, IBM Redbooks, and the like. For example, information about the QA pipeline of the IBM Watson™ cognitive system can be found in Yuan et al., "Watson and Healthcare," IBM developerWorks, 2011 and "The Era of Cognitive Systems: An Inside Look at IBM Watson and How it Works" by Rob High, IBM Redbooks, 2012.

As noted above, while the input to the cognitive system 100 from a client device may be posed in the form of a natural language question, the illustrative embodiments are not limited to such. Rather, the input question may in fact be formatted or structured as any suitable type of request which may be parsed and analyzed using structured and/or unstructured input analysis, including but not limited to the natural language parsing and analysis mechanisms of a cognitive system such as IBM Watson™, to determine the basis upon which to perform cognitive analysis and providing a result of the cognitive analysis. In the case of a healthcare based cognitive system, this analysis may involve processing patient medical records, medical guidance documentation from one or more corpora, and the like, to provide a healthcare oriented cognitive system result.

In the context of the present invention, cognitive system 100 may provide a cognitive functionality for assisting with healthcare based operations. For example, depending upon the particular implementation, the healthcare based operations may comprise patient diagnostics, medical treatment recommendation systems, medical practice management systems, personal patient care plan generation and monitoring, patient electronic medical record (EMR) evaluation for various purposes, such as for identifying patients that are suitable for a medical trial or a particular type of medical treatment, or the like. Thus, the cognitive system 100 may be a healthcare cognitive system 100 that operates in the medical or healthcare type domains and which may process requests for such healthcare operations via the request processing pipeline 108 input as either structured or unstructured requests, natural language input questions, or the like. In one illustrative embodiment, the cognitive system 100 is a medical treatment recommendation system that analyzes a patient's EMR in relation to medical guidelines and other medical documentation in a corpus of information generate a recommendation as to how to treat a medical malady or medical condition of the patient. In particular, the cognitive system 100 implements a mechanism for dynamically mining new negation triggers based on structured and unstructured knowledge in accordance with one or more of the illustrative embodiments described herein.

Figure 2:
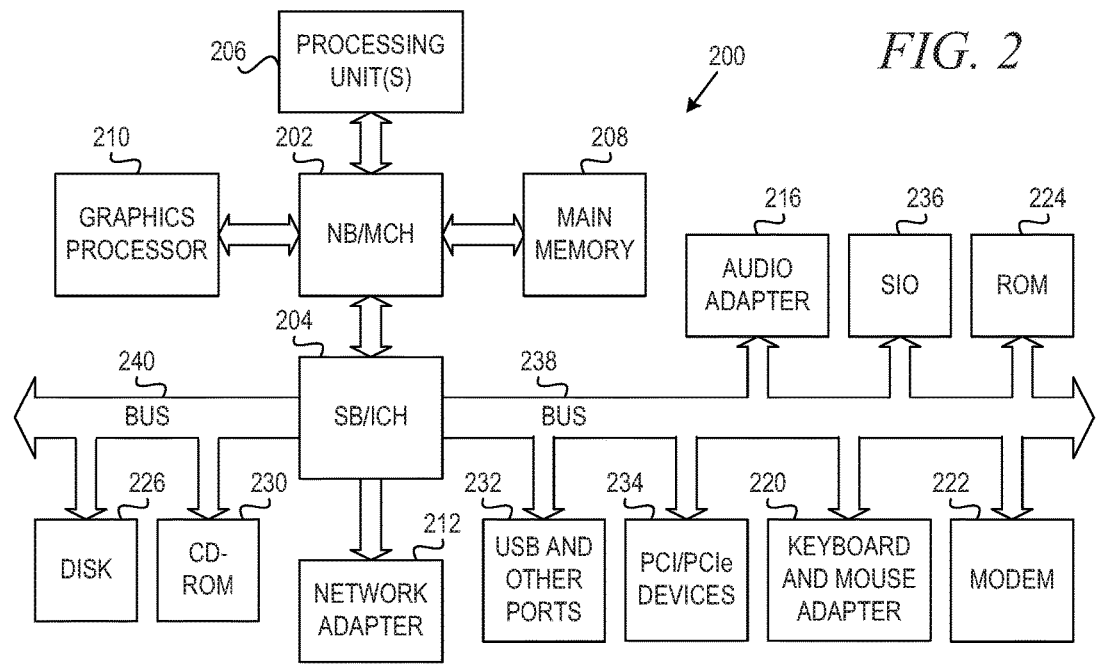
FIG. 2 is a block diagram of an example data processing system in which aspects of the illustrative embodiments are implemented.

FIG. 2 is a block diagram of an example data processing system in which aspects of the illustrative embodiments are implemented. Data processing system 200 is an example of a computer, such as server 104 or client 110 in FIG. 1, in which computer usable code or instructions implementing the processes for illustrative embodiments of the present invention are located. In one illustrative embodiment, FIG. 2 represents a server computing device, such as a server 104, which implements an NL processing system 100 and NL system pipeline 108 augmented to include the additional mechanisms of the illustrative embodiments described hereafter.

In the depicted example, data processing system 200 employs a hub architecture including north bridge and memory controller hub (NB/MCH) 202 and south bridge and input/output (I/O) controller hub (SB/ICH) 204. Processing unit 206, main memory 208, and graphics processor 210 are connected to NB/MCH 202. Graphics processor 210 is connected to NB/MCH 202 through an accelerated graphics port (AGP).

In the depicted example, local area network (LAN) adapter 212 connects to SB/ICH 204. Audio adapter 216, keyboard and mouse adapter 220, modem 222, read only memory (ROM) 224, hard disk drive (HDD) 226, CD-ROM drive 230, universal serial bus (USB) ports and other communication ports 232, and PCI/PCIe devices 234 connect to SB/ICH 204 through bus 238 and bus 240. PCI/PCIe devices may include, for example, Ethernet adapters, add-in cards, and PC cards for notebook computers. PCI uses a card bus controller, while PCIe does not. ROM 224 may be, for example, a flash basic input/output system (BIOS).

HDD 226 and CD-ROM drive 230 connect to SB/ICH 204 through bus 240. HDD 226 and CD-ROM drive 230 may use, for example, an integrated drive electronics (IDE) or serial advanced technology attachment (SATA) interface. Super I/O (SIO) device 236 is connected to SB/ICH 204.

An operating system runs on processing unit 206. The operating system coordinates and provides control of various components within the data processing system 200 in FIG. 2. As a client, the operating system is a commercially available operating system such as Microsoft® Windows 8®. An object-oriented programming system, such as the Java™ programming system, may run in conjunction with the operating system and provides calls to the operating system from Java™ programs or applications executing on data processing system 200.

As a server, data processing system 200 may be, for example, an IBM® eServer™ System P® computer system, running the Advanced Interactive Executive (AIX®) operating system or the LINUX™ operating system. Data processing system 200 may be a symmetric multiprocessor (SMP) system including a plurality of processors in processing unit 206. Alternatively, a single processor system may be employed.

Instructions for the operating system, the object-oriented programming system, and applications or programs are located on storage devices, such as HDD 226, and are loaded into main memory 208 for execution by processing unit 206. The processes for illustrative embodiments of the present invention are performed by processing unit 206 using computer usable program code, which is located in a memory such as, for example, main memory 208, ROM 224, or in one or more peripheral devices 226 and 230, for example.

A bus system, such as bus 238 or bus 240 as shown in FIG. 2, is comprised of one or more buses. Of course, the bus system may be implemented using any type of communication fabric or architecture that provides for a transfer of data between different components or devices attached to the fabric or architecture. A communication unit, such as modem 222 or network adapter 212 of FIG. 2, includes one or more devices used to transmit and receive data. A memory may be, for example, main memory 208, ROM 224, or a cache such as found in NB/MCH 202 in FIG. 2.

Those of ordinary skill in the art will appreciate that the hardware depicted in FIGS. 1 and 2 may vary depending on the implementation. Other internal hardware or peripheral devices, such as flash memory, equivalent non-volatile memory, or optical disk drives and the like, may be used in addition to or in place of the hardware depicted in FIGS. 1 and 2. Also, the processes of the illustrative embodiments may be applied to a multiprocessor data processing system, other than the SMP system mentioned previously, without departing from the spirit and scope of the present invention.

Moreover, the data processing system 200 may take the form of any of a number of different data processing systems including client computing devices, server computing devices, a tablet computer, laptop computer, telephone or other communication device, a personal digital assistant (PDA), or the like. In some illustrative examples, data processing system 200 may be a portable computing device that is configured with flash memory to provide non-volatile memory for storing operating system files and/or user-generated data, for example. Essentially, data processing system 200 may be any known or later developed data processing system without architectural limitation.

Figure 3:
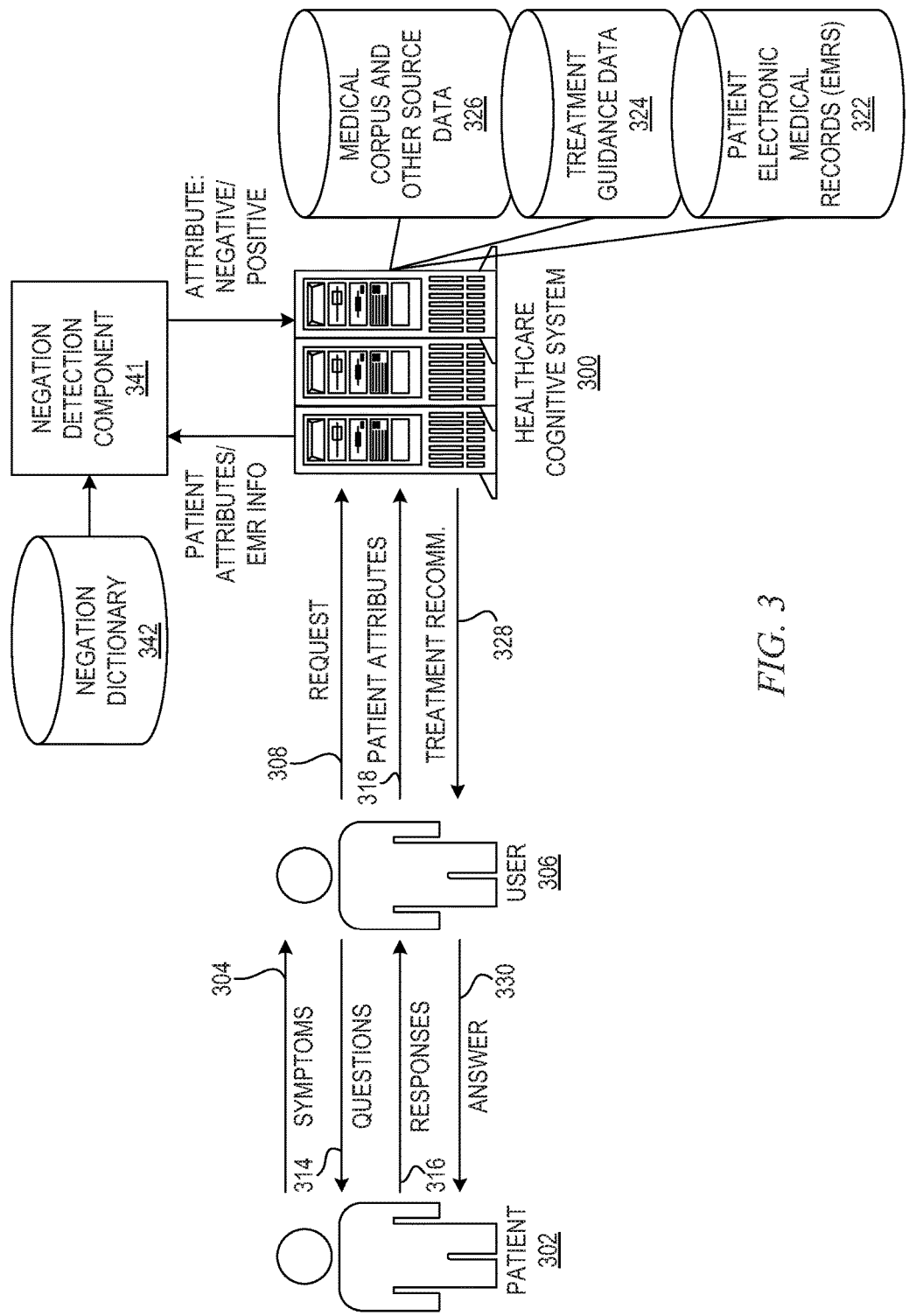
FIG. 3 is an example diagram illustrating an interaction of elements of a healthcare cognitive system in accordance with one illustrative embodiment.

FIG. 3 is an example diagram illustrating an interaction of elements of a healthcare cognitive system in accordance with one illustrative embodiment. The example diagram of FIG. 3 depicts an implementation of a healthcare cognitive system 300 that is configured to provide medical treatment recommendations for patients. However, it should be appreciated that this is only an example implementation and other healthcare operations may be implemented in other embodiments of the healthcare cognitive system 300 without departing from the spirit and scope of the present invention.

Moreover, it should be appreciated that while FIG. 3 depicts the patient 302 and user 306 as human figures, the interactions with and between these entities may be performed using computing devices, medical equipment, and/or the like, such that entities 302 and 306 may in fact be computing devices, e.g., client computing devices. For example, the interactions 304, 314, 316, and 330 between the patient 302 and the user 306 may be performed orally, e.g., a doctor interviewing a patient, and may involve the use of one or more medical instruments, monitoring devices, or the like, to collect information that may be input to the healthcare cognitive system 300 as patient attributes 318. Interactions between the user 306 and the healthcare cognitive system 300 will be electronic via a user computing device (not shown), such as a client computing device 110 or 112 in FIG. 1, communicating with the healthcare cognitive system 300 via one or more data communication links and potentially one or more data networks.

As shown in FIG. 3, in accordance with one illustrative embodiment, a patient 302 presents symptoms 304 of a medical malady or condition to a user 306, such as a healthcare practitioner, technician, or the like. The user 306 may interact with the patient 302 via a question 314 and response 316 exchanges where the user gathers more information about the patient 302, the symptoms 304, and the medical malady or condition of the patient 302. It should be appreciated that the questions/responses may in fact also represent the user 306 gathering information from the patient 302 using various medical equipment, e.g., blood pressure monitors, thermometers, wearable health and activity monitoring devices associated with the patient such as a FitBit™, a wearable heart monitor, or any other medical equipment that may monitor one or more medical characteristics of the patient 302. In some cases such medical equipment may be medical equipment typically used in hospitals or medical centers to monitor vital signs and medical conditions of patients that are present in hospital beds for observation or medical treatment.

In response, the user 302 submits a request 308 to the healthcare cognitive system 300, such as via a user interface on a client computing device that is configured to allow users to submit requests to the healthcare cognitive system 300 in a format that the healthcare cognitive system 300 can parse and process. The request 308 may include, or be accompanied with, information identifying patient attributes 318. These patient attributes 318 may include, for example, an identifier of the patient 302 from which patient EMRs 322 for the patient may be retrieved, demographic information about the patient, the symptoms 304, and other pertinent information obtained from the responses 316 to the questions 314 or information obtained from medical equipment used to monitor or gather data about the condition of the patient 302. Any information about the patient 302 that may be relevant to a cognitive evaluation of the patient by the healthcare cognitive system 300 may be included in the request 308 and/or patient attributes 318.

The healthcare cognitive system 300 provides a cognitive system that is specifically configured to perform an implementation specific healthcare oriented cognitive operation. In the depicted example, this healthcare oriented cognitive operation is directed to providing a treatment recommendation 328 to the user 306 to assist the user 306 in treating the patient 302 based on their reported symptoms 304 and other information gathered about the patient 302 via the question 314 and response 316 process and/or medical equipment monitoring/data gathering. The healthcare cognitive system 300 operates on the request 308 and patient attributes 318 utilizing information gathered from the medical corpus and other source data 326, treatment guidance data 324, and the patient EMRs 322 associated with the patient 302 to generate one or more treatment recommendation 328. The treatment recommendations 328 may be presented in a ranked ordering with associated supporting evidence, obtained from the patient attributes 318 and data sources 322-326, indicating the reasoning as to why the treatment recommendation 328 is being provided and why it is ranked in the manner that it is ranked.

For example, based on the request 308 and the patient attributes 318, the healthcare cognitive system 300 may operate on the request, such as by using a QA pipeline type processing as described herein, to parse the request 308 and patient attributes 318 to determine what is being requested and the criteria upon which the request is to be generated as identified by the patient attributes 318, and may perform various operations for generating queries that are sent to the data sources 322-326 to retrieve data, generate candidate treatment recommendations (or answers to the input question), and score these candidate treatment recommendations based on supporting evidence found in the data sources 322-326. In the depicted example, the patient EMRs 322 is a patient information repository that collects patient data from a variety of sources, e.g., hospitals, laboratories, physicians' offices, health insurance companies, pharmacies, etc. The patient EMRs 322 store various information about individual patients, such as patient 302, in a manner (structured, unstructured, or a mix of structured and unstructured formats) that the information may be retrieved and processed by the healthcare cognitive system 300. This patient information may comprise various demographic information about patients, personal contact information about patients, employment information, health insurance information, laboratory reports, physician reports from office visits, hospital charts, historical information regarding previous diagnoses, symptoms, treatments, prescription information, etc. Based on an identifier of the patient 302, the patient's corresponding EMRs 322 from this patient repository may be retrieved by the healthcare cognitive system 300 and searched/processed to generate treatment recommendations 328.

The treatment guidance data 324 provides a knowledge base of medical knowledge that is used to identify potential treatments for a patient based on the patient's attributes 318 and historical information presented in the patient's EMRs 322. This treatment guidance data 324 may be obtained from official treatment guidelines and policies issued by medical authorities, e.g., the American Medical Association, may be obtained from widely accepted physician medical and reference texts, e.g., the Physician's Desk Reference, insurance company guidelines, or the like. The treatment guidance data 324 may be provided in any suitable form that may be ingested by the healthcare cognitive system 300 including both structured and unstructured formats.

In some cases, such treatment guidance data 324 may be provided in the form of rules that indicate the criteria required to be present, and/or required not to be present, for the corresponding treatment to be applicable to a particular patient for treating a particular symptom or medical malady/condition. For example, the treatment guidance data 324 may comprise a treatment recommendation rule that indicates that for a treatment of Decitabine, strict criteria for the use of such a treatment is that the patient 302 is less than or equal to 60 years of age, has acute myeloid leukemia (AML), and no evidence of cardiac disease. Thus, for a patient 302 that is 59 years of age, has AML, and does not have any evidence in their patient attributes 318 or patient EMRs indicating evidence of cardiac disease, the following conditions of the treatment rule exist:

Age<=60 years=59 (MET);
Patient has AML=AML (MET); and
Cardiac Disease=false (MET)

Since all of the criteria of the treatment rule are met by the specific information about this patient 302, then the treatment of Decitabine is a candidate treatment for consideration for this patient 302. However, if the patient had been 69 years old, the first criterion would not have been met and the Decitabine treatment would not be a candidate treatment for consideration for this patient 302. Various potential treatment recommendations may be evaluated by the healthcare cognitive system 300 based on ingested treatment guidance data 324 to identify subsets of candidate treatments for further consideration by the healthcare cognitive system 300 by scoring such candidate treatments based on evidential data obtained from the patient EMRs 322 and medical corpus and other source data 326.

For example, data mining processes may be employed to mine the data in sources 322 and 326 to identify evidential data supporting and/or refuting the applicability of the candidate treatments to the particular patient 302 as characterized by the patient's patient attributes 318 and EMRs 322. For example, for each of the criteria of the treatment rule, the results of the data mining provides a set of evidence that supports giving the treatment in the cases where the criterion is "MET" and in cases where the criterion is "NOT MET." The healthcare cognitive system 300 processes the evidence in accordance with various cognitive logic algorithms to generate a confidence score for each candidate treatment recommendation indicating a confidence that the corresponding candidate treatment recommendation is valid for the patient 302. The candidate treatment recommendations may then be ranked according to their confidence scores and presented to the user 306 as a ranked listing of treatment recommendations 328. In some cases, only a highest ranked, or final answer, is returned as the treatment recommendation 328. The treatment recommendation 328 may be presented to the user 306 in a manner that the underlying evidence evaluated by the healthcare cognitive system 300 may be accessible, such as via a drilldown interface, so that the user 306 may identify the reasons why the treatment recommendation 328 is being provided by the healthcare cognitive system 300.

In accordance with the illustrative embodiments herein, the healthcare cognitive system 300 is augmented to operate with, implement, or include negation detection component 341 for dynamically mining new negation triggers based on structured and unstructured knowledge. While the above description describes a general healthcare cognitive system 300 that may operate on specifically configured treatment recommendation rules, the mechanisms of the illustrative embodiments modify such operations to utilize the negation detection component 341, which is medical malady independent or agnostic and operates in the manner previously described above with particular reference to FIGS. 4-7 below.

Thus, in response to the healthcare cognitive system 300 receiving the request 308 and patient attributes 318, the healthcare cognitive system 300 may retrieve the patient's EMR data from source(s) 322. This information is provided to negation detection component 341, which determines whether attributes in an EMR are negated in the text. In one example implementation, negation detection component 341 compares words in the text to a set of predetermined negation triggers in negation dictionary 342. The set of predetermined negation triggers may be compiled by subject matter experts and may include common negation words, such as "negative", or domain-specific negation triggers. In response to determining a word in the text associated with a given attribute matches a negation trigger, negation detection component 341 saves the attribute as negated. The negation dictionary may store each negation trigger in association with a particular attribute. For example, "pregnancy test" may have a different set of negation triggers than "exposure to chicken pox."

In accordance with an illustrative embodiment, a mechanism is provided in negation detection component 341 that builds a set of negation triggers using electronic medical record (EMR) data that has both structured and unstructured information about patients. The mechanism of the illustrative embodiment may be domain independent in that it does not have to be re-built for each topic; however, the illustrative embodiments assume that a set of EMRs is available and their structured information is known, to be able to build the negation dictionaries. The mechanism of the illustrative embodiment uses cohort analysis, also referred to as clustering (e.g., k-means clustering), to identify patients that are similar and compare their structured and unstructured attributes to identify which attributes could be negated, because they are not seen in similar patients, and build a negation dictionary using negated/non-negated information obtained for each attribute. The mechanism for dynamically mining new negation triggers based on structured and unstructured knowledge is described in further detail below with reference to FIGS. 4-7.

Cluster analysis or clustering is the task of grouping a set of objects in such a way that objects in the same group (called a cluster) are more similar (in some sense or another) to each other than to those in other groups (clusters). It is a main task of exploratory data mining, and a common technique for statistical data analysis, used in many fields, including machine learning, pattern recognition, image analysis, information retrieval, bioinformatics, data compression, and computer graphics.

Cluster analysis itself is not one specific algorithm, but the general task to be solved. It can be achieved by various algorithms that differ significantly in their notion of what constitutes a cluster and how to efficiently find them. Popular notions of clusters include groups with small distances among the cluster members, dense areas of the data space, intervals or particular statistical distributions. Clustering can therefore be formulated as a multi-objective optimization problem. The appropriate clustering algorithm and parameter settings (including values such as the distance function to use, a density threshold or the number of expected clusters) depend on the individual data set and intended use of the results. Cluster analysis as such is not an automatic task, but an iterative process of knowledge discovery or interactive multi-objective optimization that involves trial and failure. It is often necessary to modify data preprocessing and model parameters until the result achieves the desired properties.

While FIG. 3 is depicted with an interaction between the patient 302 and a user 306, which may be a healthcare practitioner such as a physician, nurse, physician's assistant, lab technician, or any other healthcare worker, for example, the illustrative embodiments do not require such. Rather, the patient 302 may interact directly with the healthcare cognitive system 300 without having to go through an interaction with the user 306 and the user 306 may interact with the healthcare cognitive system 300 without having to interact with the patient 302. For example, in the first case, the patient 302 may be requesting 308 treatment recommendations 328 from the healthcare cognitive system 300 directly based on the symptoms 304 provided by the patient 302 to the healthcare cognitive system 300. Moreover, the healthcare cognitive system 300 may actually have logic for automatically posing questions 314 to the patient 302 and receiving responses 316 from the patient 302 to assist with data collection for generating treatment recommendations 328. In the latter case, the user 306 may operate based on only information previously gathered and present in the patient EMR 322 by sending a request 308 along with patient attributes 318 and obtaining treatment recommendations in response from the healthcare cognitive system 300. Thus, the depiction in FIG. 3 is only an example and should not be interpreted as requiring the particular interactions depicted when many modifications may be made without departing from the spirit and scope of the present invention.

As mentioned above, the healthcare cognitive system 300 may include a request processing pipeline, such as request processing pipeline 108 in FIG. 1, which may be implemented, in some illustrative embodiments, as a Question Answering (QA) pipeline. The QA pipeline may receive an input question, such as "what is the appropriate treatment for patient P?", or a request, such as "diagnose and provide a treatment recommendation for patient P."

Figure 4:
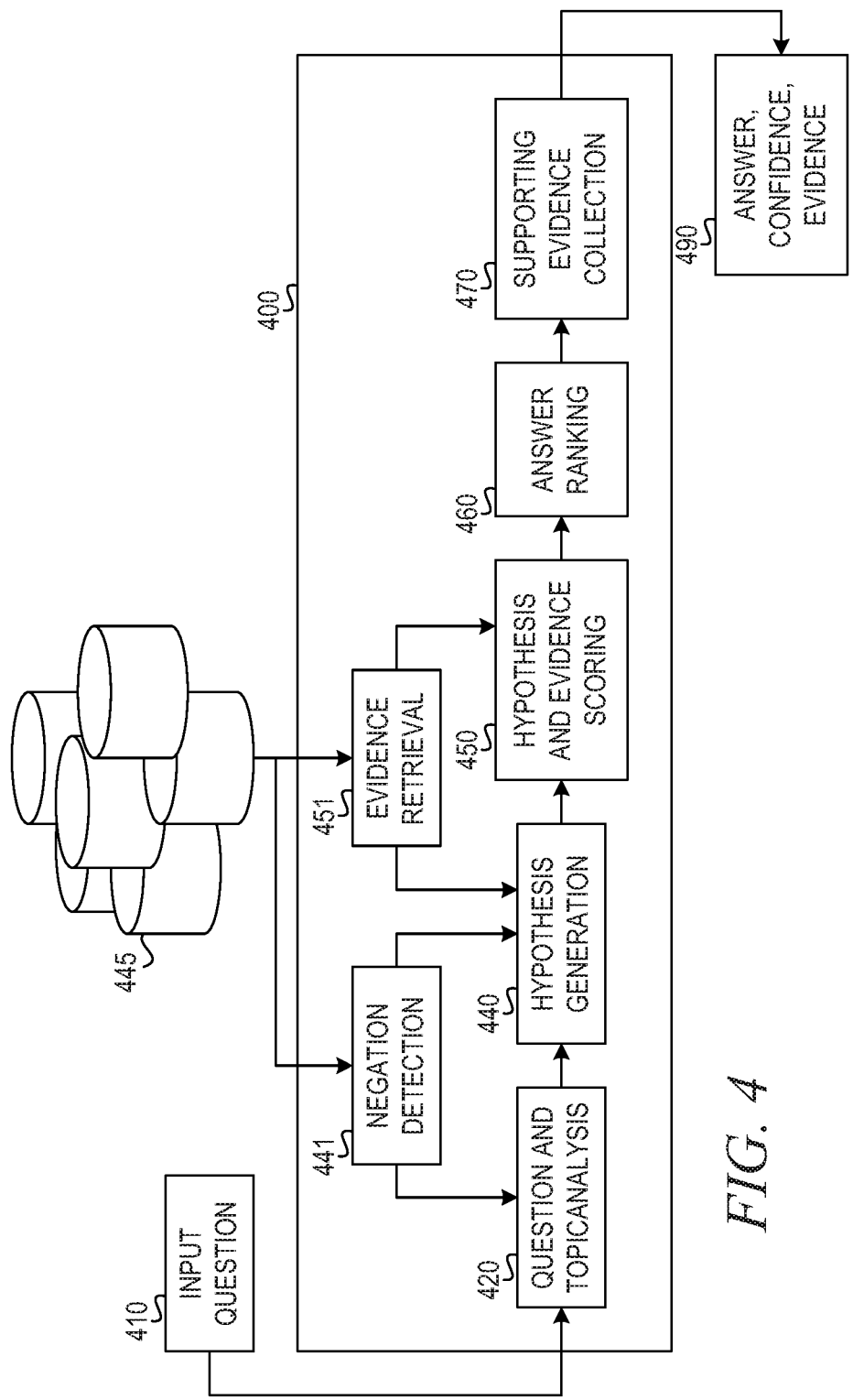
FIG. 4 illustrates a request processing pipeline for processing an input question in accordance with one illustrative embodiment.

FIG. 4 illustrates a request processing pipeline for processing an input question in accordance with one illustrative embodiment. The request processing pipeline of FIG. 4 may be implemented, for example, as request processing pipeline 108 of cognitive processing system 100 in FIG. 1. It should be appreciated that the stages of the request processing pipeline shown in FIG. 4 are implemented as one or more software engines, components, or the like, which are configured with logic for implementing the functionality attributed to the particular stage. Each stage is implemented using one or more of such software engines, components or the like. The software engines, components, etc. are executed on one or more processors of one or more data processing systems or devices and utilize or operate on data stored in one or more data storage devices, memories, or the like, on one or more of the data processing systems. The request processing pipeline of FIG. 4 is augmented, for example, in one or more of the stages to implement the improved mechanism of the illustrative embodiments described hereafter, additional stages may be provided to implement the improved mechanism, or separate logic from the pipeline 400 may be provided for interfacing with the pipeline 400 and implementing the improved functionality and operations of the illustrative embodiments.

In the depicted example, request processing pipeline 400 is implemented in a Question Answering (QA) system. The description that follows refers to the cognitive system pipeline or request processing pipeline as a QA system; however, aspects of the illustrative embodiments may be applied to other request processing systems, such as Web search engines that return semantic passages from a corpus of documents.

As shown in FIG. 4, the request processing pipeline 400 comprises a plurality of stages 410-490 through which the cognitive system operates to analyze an input question and generate a final response. In an initial question input stage, the QA system receives an input question 410 that is presented in a natural language format. That is, user inputs, via a user interface, an input question for which the user wishes to obtain an answer, e.g., "What medical treatments for diabetes are applicable to a 60 year old patient with cardiac disease?" In response to receiving the input question 410, the next stage of the QA system pipeline 400, i.e. the question and topic analysis stage 420, analyzes the input question using natural language processing (NLP) techniques to extract major elements from the input question, and classify the major elements according to types, e.g., names, dates, or any of a plethora of other defined topics. For example, in the example question above, the term "who" may be associated with a topic for "persons" indicating that the identity of a person is being sought, "Washington" may be identified as a proper name of a person with which the question is associated, "closest" may be identified as a word indicative of proximity or relationship, and "advisors" may be indicative of a noun or other language topic. Similarly, in the previous question "medical treatments" may be associated with pharmaceuticals, medical procedures, holistic treatments, or the like, "diabetes" identifies a particular medical condition, "60 years old" indicates an age of the patient, and "cardiac disease" indicates an existing medical condition of the patient.

In addition, the extracted major features include key words and phrases classified into question characteristics, such as the focus of the question, the lexical answer type (LAT) of the question, and the like. As referred to herein, a lexical answer type (LAT) is a word in, or a word inferred from, the input question that indicates the type of the answer, independent of assigning semantics to that word. For example, in the question "What maneuver was invented in the 1500s to speed up the game and involves two pieces of the same color?," the LAT is the string "maneuver." The focus of a question is the part of the question that, if replaced by the answer, makes the question a standalone statement. For example, in the question "What drug has been shown to relieve the symptoms of attention deficit disorder with relatively few side effects?," the focus is "What drug" since if this phrase were replaced with the answer it would generate a true sentence, e.g., the answer "Adderall" can be used to replace the phrase "What drug" to generate the sentence "Adderall has been shown to relieve the symptoms of attention deficit disorder with relatively few side effects." The focus often, but not always, contains the LAT. On the other hand, in many cases it is not possible to infer a meaningful LAT from the focus.

Referring again to FIG. 4, the identified major elements of the question are then used during a hypothesis generation stage 440 to decompose the question into one or more search queries that are applied to the corpora of data/information 445 in order to generate one or more hypotheses. The queries are applied to one or more text indexes storing information about the electronic texts, documents, articles, websites, and the like, that make up the corpus of data/information, e.g., the corpus of data 106 in FIG. 1. The queries are applied to the corpus of data/information at the hypothesis generation stage 440 to generate results identifying potential hypotheses for answering the input question, which can then be evaluated. That is, the application of the queries results in the extraction of portions of the corpus of data/information matching the criteria of the particular query. These portions of the corpus are then analyzed and used in the hypothesis generation stage 440, to generate hypotheses for answering the input question 410. These hypotheses are also referred to herein as "candidate answers" for the input question. For any input question, at this stage 440, there may be hundreds of hypotheses or candidate answers generated that may need to be evaluated.

Negation detection component 441 determines whether attributes in the input 410 or in documents within corpora 445 are negated in the text. In one example implementation, negation detection component 441 compares words in the text to a set of predetermined negation triggers. The set of predetermined negation triggers, also referred to as a negation dictionary, may be compiled by subject matter experts and may include common negation words, such as "negative", or domain-specific negation triggers. In response to determining a word in the text associated with a given attribute matches a negation trigger, negation detection component 441 saves the attribute as negated. The negation dictionary may store each negation trigger in association with a particular attribute. The negation/non-negation of an attribute may be referred to as a feature of the input 410 or document within corpora 445.

In accordance with an illustrative embodiment, a mechanism is provided that builds a set of negation triggers using electronic medical record (EMR) data that has both structured and unstructured information about patients. The mechanism of the illustrative embodiment may be domain independent in that it does not have to be re-built for each topic; however, the illustrative embodiments assume that a set of EMRs is available and their structured information is known, to be able to build the negation dictionaries. The mechanism of the illustrative embodiment uses cohort analysis, also referred to as clustering (e.g., k-means clustering), to identify patients that are similar and compare their structured and unstructured attributes to identify which attributes could be negated, because they are not seen in similar patients, and build a negation dictionary using negated/non-negated information obtained for each attribute. The mechanism for dynamically mining new negation triggers based on structured and unstructured knowledge is described in further detail below with reference to FIGS. 5-7.

The QA system pipeline 400, in stage 450, then performs a deep analysis and comparison of the language of the input question and the language of each hypothesis or "candidate answer," as well as performs evidence scoring to evaluate the likelihood that the particular hypothesis is a correct answer for the input question. This involves evidence retrieval 451, which retrieves passages from corpora 445. Hypothesis and evidence scoring phase 450 uses a plurality of scoring algorithms, each performing a separate type of analysis of the language of the input question and/or content of the corpus that provides evidence in support of, or not in support of, the hypothesis. Each scoring algorithm generates a score based on the analysis it performs which indicates a measure of relevance of the individual portions of the corpus of data/information extracted by application of the queries as well as a measure of the correctness of the corresponding hypothesis, i.e. a measure of confidence in the hypothesis. There are various ways of generating such scores depending upon the particular analysis being performed. In general, however, these algorithms look for particular terms, phrases, or patterns of text that are indicative of terms, phrases, or patterns of interest and determine a degree of matching with higher degrees of matching being given relatively higher scores than lower degrees of matching.

For example, an algorithm may be configured to look for the exact term from an input question or synonyms to that term in the input question, e.g., the exact term or synonyms for the term "movie," and generate a score based on a frequency of use of these exact terms or synonyms. In such a case, exact matches will be given the highest scores, while synonyms may be given lower scores based on a relative ranking of the synonyms as may be specified by a subject matter expert (person with knowledge of the particular domain and terminology used) or automatically determined from frequency of use of the synonym in the corpus corresponding to the domain. Thus, for example, an exact match of the term "movie" in content of the corpus (also referred to as evidence, or evidence passages) is given a highest score. A synonym of movie, such as "motion picture" may be given a lower score but still higher than a synonym of the type "film" or "moving picture show." Instances of the exact matches and synonyms for each evidence passage may be compiled and used in a quantitative function to generate a score for the degree of matching of the evidence passage to the input question.

Thus, for example, a hypothesis or candidate answer to the input question of "What was the first movie?" is "The Horse in Motion." If the evidence passage contains the statements "The first motion picture ever made was 'The Horse in Motion' in 1878 by Eadweard Muybridge. It was a movie of a horse running," and the algorithm is looking for exact matches or synonyms to the focus of the input question, i.e. "movie," then an exact match of "movie" is found in the second sentence of the evidence passage and a highly scored synonym to "movie," i.e. "motion picture," is found in the first sentence of the evidence passage. This may be combined with further analysis of the evidence passage to identify that the text of the candidate answer is present in the evidence passage as well, i.e. "The Horse in Motion." These factors may be combined to give this evidence passage a relatively high score as supporting evidence for the candidate answer "The Horse in Motion" being a correct answer.

It should be appreciated that this is just one simple example of how scoring can be performed. Many other algorithms of various complexities may be used to generate scores for candidate answers and evidence without departing from the spirit and scope of the present invention.

In answer ranking stage 460, the scores generated by the various scoring algorithms are synthesized into confidence scores or confidence measures for the various hypotheses. This process involves applying weights to the various scores, where the weights have been determined through training of the statistical model employed by the QA system and/or dynamically updated. For example, the weights for scores generated by algorithms that identify exactly matching terms and synonyms may be set relatively higher than other algorithms that evaluate publication dates for evidence passages.

The weighted scores are processed in accordance with a statistical model generated through training of the QA system that identifies a manner by which these scores may be combined to generate a confidence score or measure for the individual hypotheses or candidate answers. This confidence score or measure summarizes the level of confidence that the QA system has about the evidence that the candidate answer is inferred by the input question, i.e. that the candidate answer is the correct answer for the input question.

The resulting confidence scores or measures are processed by answer ranking stage 460, which compares the confidence scores and measures to each other, compares them against predetermined thresholds, or performs any other analysis on the confidence scores to determine which hypotheses/candidate answers are the most likely to be the correct answer to the input question. The hypotheses/candidate answers are ranked according to these comparisons to generate a ranked listing of hypotheses/candidate answers (hereafter simply referred to as "candidate answers").

Supporting evidence collection phase 470 collects evidence that supports the candidate answers from answer ranking phase 460. From the ranked listing of candidate answers in stage 460 and supporting evidence from supporting evidence collection stage 470, NL system pipeline 400 generates a final answer, confidence score, and evidence 480, or final set of candidate answers with confidence scores and supporting evidence, and outputs answer, confidence, and evidence 490 to the submitter of the original input question 410 via a graphical user interface or other mechanism for outputting information.

Figure 5:
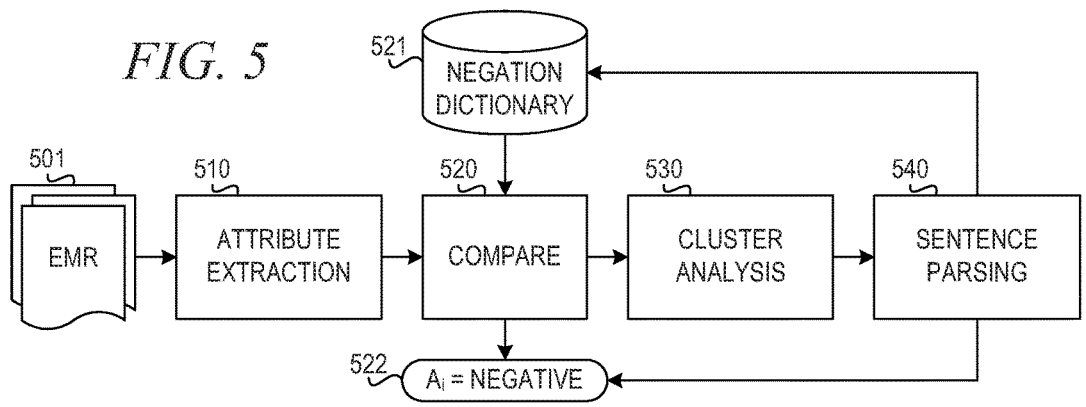
FIG. 5 depicts an example block diagram of a mechanism for dynamically mining new negation triggers based on structured and unstructured knowledge in accordance with an illustrative embodiment.

FIG. 5 depicts an example block diagram of a mechanism for dynamically mining new negation triggers based on structured and unstructured knowledge in accordance with an illustrative embodiment. Electronic medical records (EMRs) 501 are provided to attribute extraction component 510, which extracts attributes of interest from each sentence S; using noun phrases and Unified Medical Language System (UMLS) dictionary, for example. The UMLS is a compendium of many controlled vocabularies in the biomedical sciences. It provides a mapping structure among these vocabularies and, thus, allows one to translate among the various terminology systems; it may also be viewed as a comprehensive thesaurus and ontology of biomedical concepts. UMLS further provides facilities for natural language processing. It is intended to be used mainly by developers of systems in medical informatics.

Compare component 520 identifies whether each attribute $A_i$ is negated or not by comparing each adjective defining the attribute in question to negation dictionary 521. In response to a given attribute $A_i$ having an adjective or other associated word in the text that matches a negation trigger in negation dictionary 521, compare component saves the attribute as negated ($A_i$=NEGATIVE).

In response to compare component 520 determining the given attribute does not have an adjective or other associated word that matches a negation trigger in negation dictionary 521, cluster analysis component 530 performs dynamic cluster analysis to form clusters of patients that are similar to the current patient (current EMR 501) considering both structured and unstructured data. Cluster analysis component 530 determines whether the attribute $A_i$ is mostly seen positive or negative from the closest cluster C. If the most recent data about attribute $A_i$ is mostly negative, sentence parsing component 540 identifies negation triggers in sentence $S_i$.

To identify negation triggers in sentence $S_i$, sentence parsing component 540 draws a parse tree of $S_i$ and for every adjective that defines $A_i$, adds the adjective a to the list of negation triggers in negation dictionary 521 and saves $A_i$ as negated ($A_i$=NEGATIED) 522.

As an example, consider the sentence, "She has negative pregnancy test," where "negative" may already be in the negation dictionary because it is a widely used negation trigger. However, for the sentence, "She has a clear pregnancy test," it is likely that "clear" would not be in the predetermined set of triggers. Because the mechanism does not know whether "clear" is a negation trigger or not, the mechanism does not know how to accept the "pregnancy test" attribute (negative/positive).

The mechanism of the illustrative embodiment builds a cluster set using both structured and unstructured information from the EMR data, where the closest cluster to the current patient in the attribute space is the set of patients that are the most similar to the patient (like a nearest neighbor algorithm in machine learning). In one embodiment, the mechanism uses an attribute space that is a subset of attributes related to the attribute in question. For example, the mechanism may start with ontology to determine the set of related concepts. More particularly, the mechanism may consider all attributes a number (n) of hops away from the attribute in the ontology. The number n may be adjusted in training. The mechanism considers synonyms and normalized concepts (sometimes these are in the ontology, sometimes they are a normalization). For example, pregnancy test, pregnant test, "with child", hCG test (human chorionic gonadotropin, child conception). These attributes would be all clustered, and a "clear child conception test" would make "clear" negative based on the cluster results for pregnancy.

For example, the attribute or concept for "pregnancy test" can be defined in the natural language text as "pregnancy test," "child conception test," "pregnancy," "hCG test," "pregnancy results," "pregnancy reading." This attribute could be normalized to a single concept "pregnancy test" with one of the values being pregnant/not-pregnant. The adjectives that modify the concept can be "clear," "red," "faint," "bright line." Another example of an attribute that can be is "pap smear test" or "pap test," which would have the same negation attribute as "clear." For "pregnancy test" a set of cluster attributes are the similar concepts and the set of labs ran for pregnancy like hCG test, cystic fibrosis, gestational diabetes, fetal DNA.

For the following sentence, comorbidities should be negated. By looking at the patients in the cluster, it can be seen that patients in the cluster do not generally have neuropathy, therefore "denies any history of" could be added as a negation trigger for neuropathy attribute.

"She denies any history of peripheral neuropathy."

For surgeries and treatments, different sets of triggers apply. Consider the following sentence:

"He was deemed not a suitable candidate for chemotherapy."

By analyzing the patients similar to the current patient and concluding that most of them did not have chemotherapy, chemotherapy=no can be derived and "not a suitable candidate for" can be added to the set of triggers for treatment-related attributes.

For the following sentence, "negative" is a negation trigger, showing there is no metastatic disease. This trigger cannot be used for some other attributes, such as "hearing loss" because "negative hearing loss" is not a pattern seen in natural language. Therefore, using customized set of triggers per attribute and verifying those triggers with patients that are similar is a more accurate approach than treating all attributes and all triggers the same.

"The tumor invaded muscularis proprium but there was no lymphovascular or perineural invasion and 14 resected lymph nodes were negative for metastatic disease, with a final pathologic staging of pT2N0."

Below are three more sentences with different negation triggers:

"There was no definite evidence of lymphovascular invasion"

"It was moderately differentiated without lymphovascular invasion, large venous invasion and perineural invasion present."

"No obvious evidence of pancreatic adenocarcinoma."

For the following sentence, "without a positive margin" should be negated and should be normalized to "negative margin", requiring customized negation handling for cancer patients.

"Otherwise, I do not think that without a positive margin, as well as given the good surgery that she seems to have had, that the benefit of radiation, as opposed to the remaining two months of chemotherapy, is there."

The mechanism of the illustrative embodiment then uses the closest cluster C to analyze the structured attribute of interest (pregnancy test=positive/negative) for the patients in the cluster C. The mechanism calculates the percentage (X) of patients in C that has the attribute of interest (pregnancy test=negative). The mechanism then searches for the attribute value with the most recent date. If X>T (if the percentage of patients that has a negative pregnancy test is larger than a predetermined threshold T), then most of the similar patients had a negative pregnancy test. The mechanism then looks for a new negation trigger in the current patient EMR.

Figure 6:
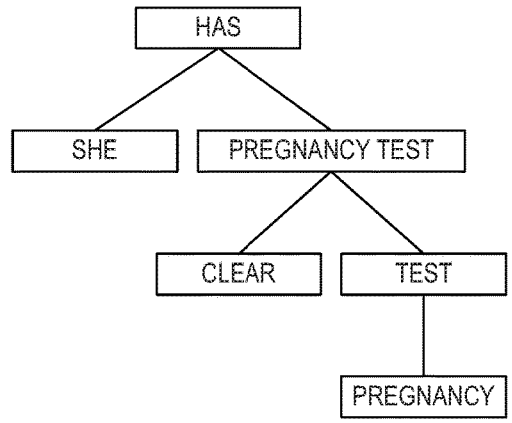
FIG. 6 illustrates an example parse tree in accordance with an illustrative embodiment.

The mechanism of the illustrative embodiment builds the parse tree of the current sentence and searches for adjectives or other modifiers that define the noun phrase "pregnancy test." FIG. 6 illustrates an example parse tree in accordance with an illustrative embodiment. If a found adjective is not found in the negation dictionary, then the mechanism adds the found adjective to the negation dictionary. The negation dictionary may store each negation trigger in association with a particular attribute. In FIG. 6, the "clear" node is an adjective defining "pregnancy test": therefore, the word "clear" is added to the list of negation triggers backed by the dynamic cluster analysis.

The mechanism described above with reference to FIGS. 5 and 6 may be implemented in pre-processing of electronic medical records or documents in the corpus or in training of a negation detection component. To train a negation detection component for a particular domain or data set, the mechanism of the illustrative embodiment may process a labeled training set with attributes labeled as negative/positive (or negative/non-negative). The mechanism may then determine the accuracy of identifying negation triggers and one may adjust parameters of cluster analysis, the number of hops to consider in the ontology, or the threshold.

In another example embodiment, the mechanism for dynamically mining new negation triggers based on structured and unstructured knowledge may be incorporated into the negation detection component (e.g., 441 in FIG. 4) to perform dynamic, real-time building of the negation dictionary. This allows the negation detection component to mine new negation triggers as more documents are processed or as new terminology is incorporated into the document texts.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

Figure 7:
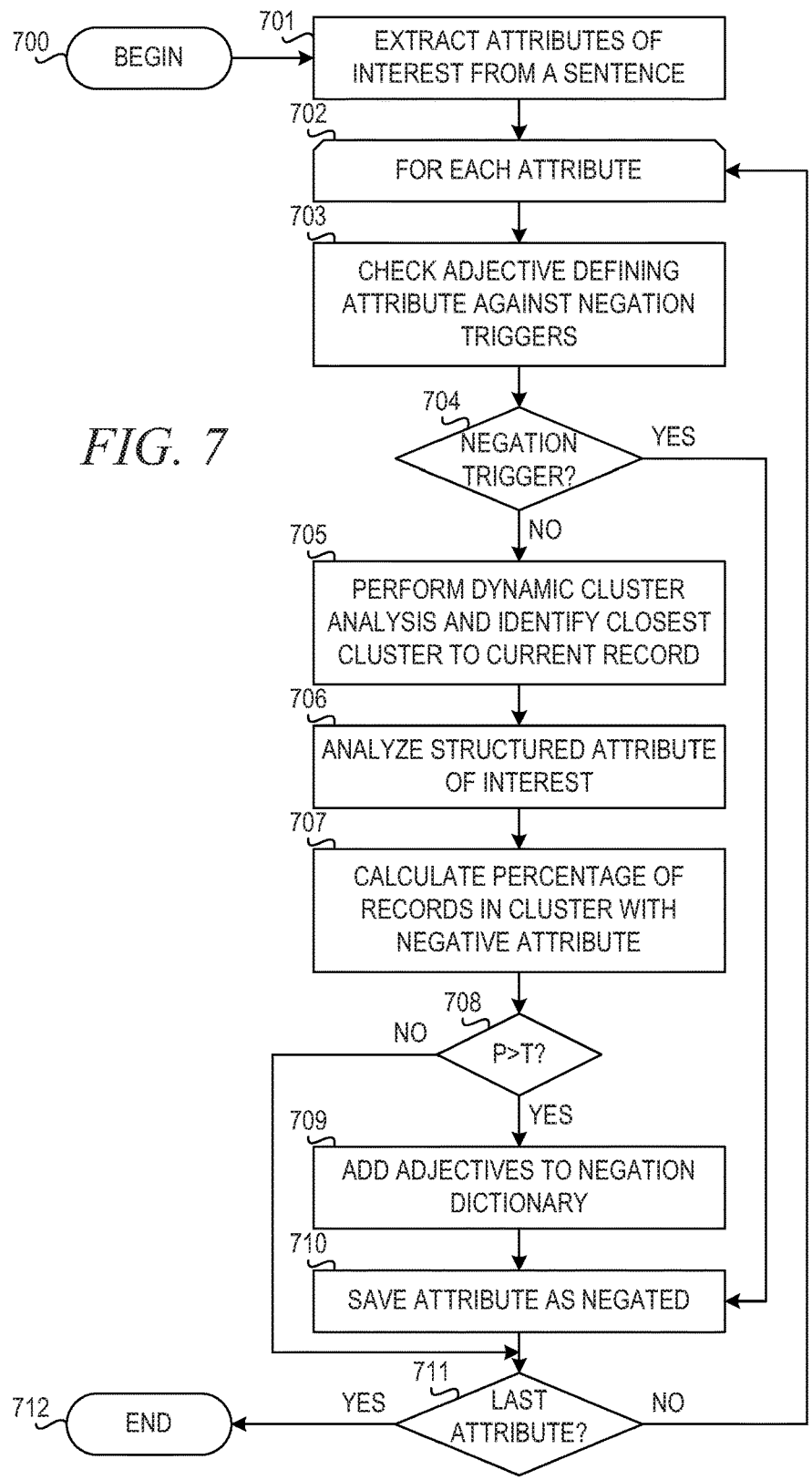
FIG. 7 is a flowchart illustrating operation of a mechanism for dynamically mining new negation triggers based on structured and unstructured knowledge in accordance with an illustrative embodiment.

FIG. 7 is a flowchart illustrating operation of a mechanism for dynamically mining new negation triggers based on structured and unstructured knowledge in accordance with an illustrative embodiment. Operation begins processing for a given sentence $S_i$ (block 700), and the mechanism extracts attributes of interest from sentence $S_i$ (block 701). For each attribute $A_j$ (block 702), the mechanism checks each adjective or other modifier defining the attribute against a set of negation triggers (block 703). The mechanism determines whether an adjective or other modifier is a known negation trigger (block 704). If an adjective or other modifier is a known negation trigger, then operation proceeds to block 710 to save the attribute as negated ($A_j$=NEGATIVE). Thereafter, the mechanism determines whether the attribute is the last attribute in the sentence $S_i$(block 711). If the attribute is not the last attribute, then operation returns to block 702 to consider the next attribute in sentence $S_i$; otherwise, operation ends (block 712). Operation may begin again in block 700 for the next sentence $S_i$ in a given record.

If an adjective or other modifier is not a known negation trigger in block 704, then the mechanism performs dynamic cluster analysis and identifies a closest cluster C to the current record (block 705). The mechanism analyzes the structured attribute $A_j$ of interest for the records in the cluster C (block 706). The mechanism calculates a percentage P of records in the cluster C with a negative attribute $A_j$ (block 707) and determines whether the percentage P is greater than a predetermined threshold T (block 708). If the percentage P is not greater than the threshold T, then operation proceeds to block 711 to determine whether the current attribute $A_j$ is the last attribute in the sentence $S_i$.

If the percentage P is greater than the threshold T in block 708, then the mechanism adds the adjectives or other modifiers defining the attribute $A_j$ to the negation dictionary (block 709). The mechanism then saves the attribute as negated ($A_j$=NEGATIVE) (block 710). Thereafter, the mechanism determines whether the attribute is the last attribute in the sentence $S_i$ (block 711). If the attribute is not the last attribute, then operation returns to block 702 to consider the next attribute in sentence $S_i$; otherwise, operation ends (block 712). Operation may begin again in block 700 for the next sentence $S_i$ in a given record.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Thus, the illustrative embodiments provide a mechanism for dynamically mining new negation triggers based on structured and unstructured knowledge. The mechanism of the illustrative embodiments uses cohort or cluster analysis to identify patients that are similar and compare the structured and unstructured attributes to identify which attributes are likely to be negated because they are not seen in similar patients. The illustrative embodiments do not rely on a limited set of negation triggers that are predetermined manually, which is time-consuming to collect. Rather the illustrative embodiments dynamically add new negation triggers to the negation dictionary using the negated/non-negated information obtained from the closest cluster to the current patient.

As noted above, it should be appreciated that the illustrative embodiments may take the form of an entirely hardware embodiment, an entirely software embodiment or an embodiment containing both hardware and software elements. In one example embodiment, the mechanisms of the illustrative embodiments are implemented in software or program code, which includes but is not limited to firmware, resident software, microcode, etc.

A data processing system suitable for storing and/or executing program code will include at least one processor coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution.

Input/output or I/O devices (including but not limited to keyboards, displays, pointing devices, etc.) can be coupled to the system either directly or through intervening I/O controllers. Network adapters may also be coupled to the system to enable the data processing system to become coupled to other data processing systems or remote printers or storage devices through intervening private or public networks. Modems, cable modems and Ethernet cards are just a few of the currently available types of network adapters.

The description of the present invention has been presented for purposes of illustration and description, and is not intended to be exhaustive or limited to the invention in the form disclosed. Many modifications and variations will be apparent to those of ordinary skill in the art without departing from the scope and spirit of the described embodiments. The embodiment was chosen and described in order to best explain the principles of the invention, the practical application, and to enable others of ordinary skill in the art to understand the invention for various embodiments with various modifications as are suited to the particular use contemplated. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method, in a data processing system comprising at least one processor and at least one memory, the at least one memory comprising instructions executed by the at least one processor to cause the at least one processor to implement a negation detection component within a cognitive natural language processing system, the method comprising:
    analyzing, by an attribute extraction component executing within the negation detection component, a portion of natural language text to identify an attribute specified in the natural language text, wherein the portion of natural language text comprises natural language text present in an electronic medical record of a patient and wherein the attribute is a medical attribute of the patient;
    analyzing, by a compare component executing within the negation detection component, the portion of natural language text to determine whether a known negation trigger is present in the natural language text in association with the attribute;
    in response to determining that the natural language text does not contain a known negation trigger in association with the attribute, determining, by a sentence parsing component executing within the negation detection component, whether the attribute is negated based on instances of the attribute in other natural language content similar to the natural language text, comprising performing, by a clustering component executing within the negation detection component, cluster analysis to identify a cluster of entities having similar characteristics, wherein at least one entity in the cluster is associated with the natural language text, and wherein the other natural language content comprises a plurality of natural language content, each associated with a different entity in the cohort, wherein the entities of the cluster are other patients having at least one similar attribute to the patient and wherein the natural language content associated with the other patients in the cluster are electronic medical records of other patients;
    in response to determining that the attribute is negated, identifying, by the sentence parsing component, a new negation trigger associated with the attribute in the natural language text; and
    storing, by the negation detection component, the new negation trigger in association with the attribute in a negation trigger dictionary data structure.

2. The method of claim 1, further comprising adjusting parameters of the cluster analysis.

3. The method of claim 1, wherein identifying the negation trigger comprises:
    determining, by the negation detection component, for the other natural language content associated with entities in the cluster, whether instances of the attribute are specified in the natural language content in a negative context or positive context; and
    in response to a determination that a percentage of instances in the natural language content associated with the entities of the cluster is greater than a threshold, identifying, by the negation detection component, the new negation trigger associated with the attribute in the portion of natural language text.

4. The method of claim 3, wherein identifying the negation trigger further comprises:
    identifying a most recent instance of the attribute in the other natural language content which is associated with a negative context; and
    extracting a phrase or term associated with the instance of the attribute in the negative context as the negation trigger.

5. The method of claim 3, further comprising adjusting the threshold and specifying a domain.

6. The method of claim 1, wherein identifying the cluster of entities having similar characteristics comprises:
    identifying a set of attributes related to the attribute; and
    performing cluster analysis on the plurality of natural language content based on a set of attributes related to the attribute.

7. The method of claim 6, wherein identifying the set of attributes comprises identifying attributes that are a number of hops away from the attribute in ontology, a synonym for the attribute, or a normalized concept unique identifier for the attribute.

8. The method of claim 7, further comprising adjusting the number of hops.

9. A computer program product comprising a non-transitory computer readable storage medium having a computer readable program stored therein, wherein the computer readable program comprises instructions, which when executed on a processor of a computing device causes the computing device to implement a negation detection component within a cognitive natural language processing system, wherein the computer readable program causes the computing device to:
    analyze, by an attribute extraction component executing within the negation detection component, a portion of natural language text to identify an attribute specified in the natural language text, wherein the portion of natural language text comprises natural language text present in an electronic medical record of a patient and wherein the attribute is a medical attribute of the patient;
    analyze, by a compare component executing within the negation detection component, the portion of natural language text to determine whether a known negation trigger is present in the natural language text in association with the attribute;

in response to determining that the natural language text does not contain a known negation trigger in association with the attribute, determine, by a sentence parsing component executing within the negation detection component, whether the attribute is negated based on instances of the attribute in other natural language content similar to the natural language text, comprising performing, by a clustering component executing within the negation detection component, cluster analysis to identify a cluster of entities having similar characteristics, wherein at least one entity in the cluster is associated with the natural language text, and wherein the other natural language content comprises a plurality of natural language content, each associated with a different entity in the cohort, wherein the entities of the cluster are other patients having at least one similar attribute to the patient and wherein the natural language content associated with the other patients in the cluster are electronic medical records of other patients;

in response to determining that the attribute is negated, identify, by the sentence parsing component, a new negation trigger associated with the attribute in the natural language text; and store, by the negation detection component, the new negation trigger in association with the attribute in a negation trigger dictionary data structure.

10. The computer program product of claim 9, wherein identifying the negation trigger comprises:

determining, by the negation detection component, for the other natural language content associated with entities in the cluster, whether instances of the attribute are specified in the natural language content in a negative context or positive context; and in response to a determination that a percentage of instances in the natural language content associated with the entities of the cluster is greater than a threshold, identifying, by the negation detection component, the new negation trigger associated with the attribute in the portion of natural language text.

11. The computer program product of claim 9, wherein identifying the cluster of entities having similar characteristics comprises:

identifying a set of attributes related to the attribute; and
performing cluster analysis on the plurality of natural language content based on a set of attributes related to the attribute.

12. A computing device comprising:
a processor, and
a memory coupled to the processor, wherein the memory comprises instructions, which when executed on a processor of a computing device causes the computing device to implement a negation detection component within a cognitive natural language processing system, wherein the instructions cause the processor to:
analyze, by an attribute extraction component executing within the negation detection component, a portion of natural language text to identify an attribute specified in the natural language text, wherein the portion of natural language text comprises natural language text present in an electronic medical record of a patient and wherein the attribute is a medical attribute of the patient;

analyze, by a compare component executing within the negation detection component, the portion of natural language text to determine whether a known negation trigger is present in the natural language text in association with the attribute;

in response to determining that the natural language text does not contain a known negation trigger in association with the attribute, determine, by a sentence parsing component executing within the negation detection component, whether the attribute is negated based on instances of the attribute in other natural language content similar to the natural language text, comprising performing, by a clustering component executing within the negation detection component, cluster analysis to identify a cluster of entities having similar characteristics, wherein at least one entity in the cluster is associated with the natural language text, and wherein the other natural language content comprises a plurality of natural language content, each associated with a different entity in the cohort, wherein the entities of the cluster are other patients having at least one similar attribute to the patient and wherein the natural language content associated with the other patients in the cluster are electronic medical records of other patients;

in response to determining that the attribute is negated, identify, by the sentence parsing component, a new negation trigger associated with the attribute in the natural language text; and store, by the negation detection component, the new negation trigger in association with the attribute in a negation trigger dictionary data structure.

13. The computing device of claim 12, wherein identifying the negation trigger comprises:

determining, by the negation detection component, for the other natural language content associated with entities in the cluster, whether instances of the attribute are specified in the natural language content in a negative context or positive context; and in response to a determination that a percentage of instances in the natural language content associated with the entities of the cluster is greater than a threshold, identifying, by the negation detection component, the new negation trigger associated with the attribute in the portion of natural language text.

14. The computing device of claim 12, wherein identifying the cluster of entities having similar characteristics comprises:

identifying a set of attributes related to the attribute; and
performing cluster analysis on the plurality of natural language content based on a set of attributes related to the attribute.

* * * * *